(12) United States Patent
Webber (10) Patent No.: US 9,700,385 B2
(45) Date of Patent: Jul. 11, 2017

(54) ATTACHMENT STRUCTURE

(71) Applicant: Align Technology, Inc., San Jose, CA (US)

(72) Inventor: Peter Webber, Layfayette, CA (US)

(73) Assignee: Alitn Technology, Inc., San Jose, CA (US)

( * ) Notice: Subject to any disclaimer, the term of this patent is extended or adjusted under 35 U.S.C. 154(b) by 287 days.

(21) Appl. No.: 14/466,734

(22) Filed: Aug. 22, 2014

(65) Prior Publication Data
US 2016/0051341 A1 Feb. 25, 2016

(51) Int. Cl.
A61C 3/00 (2006.01)
A61C 7/12 (2006.01)
A61C 7/00 (2006.01)
A61C 7/08 (2006.01)

(52) U.S. Cl.
CPC ............... *A61C 7/12* (2013.01); *A61C 7/002* (2013.01); *A61C 7/08* (2013.01)

(58) Field of Classification Search
CPC .............. A61C 7/12; A61C 7/002; A61C 7/08
See application file for complete search history.

(56) References Cited

U.S. PATENT DOCUMENTS

| 8,439,672 | B2 | 5/2013 | Matov et al. |
| 9,107,722 | B2 * | 8/2015 | Matov ...................... A61C 7/00 |
| 9,433,476 | B2 * | 9/2016 | Khardekar .............. G06F 17/50 |
| 2013/0034822 | A1 | 2/2013 | Teasdale |
| 2013/0230818 | A1 | 9/2013 | Matov et al. |
| 2016/0310236 | A1 * | 10/2016 | Kopelman ............. A61C 7/002 |

* cited by examiner

*Primary Examiner* — Glenn Richman
(74) *Attorney, Agent, or Firm* — Brooks, Cameron & Huebsch, PLLC (57) ABSTRACT

A series of appliances including a first shell and a second shell can be designed to incrementally implement a treatment plan. The first and second shells can have cavities designed to receive teeth of a jaw. The first shell can be designed to interface with a first surface of a plurality of surfaces of an attachment structure to provide a first engagement force specific to a first stage of the treatment plan. The second shell can be designed to interface with a second surface of the plurality of surfaces of the attachment structure attached to the at least one tooth of the first jaw to provide a second engagement force specific to a second stage of the treatment plan.

20 Claims, 8 Drawing Sheets

ATTACHMENT STRUCTURE

BACKGROUND

The present disclosure is related generally to the field of dental treatment. More particularly, the present disclosure is related to systems, methods, computing device readable media, and devices for attachment structures.

Dental treatments may involve, for instance, restorative and/or orthodontic procedures. Restorative procedures may be designed to implant a dental prosthesis (e.g., a crown, bridge inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning dental appliances for realigning teeth. Such appliances may utilize a thin shell of light weight and/or transparent material having resilient properties, referred to as an "aligner," that generally conforms to a patient's teeth but is slightly out of alignment with a current tooth configuration.

An example of orthodontic repositioning that can occur through a dental process is a process that uses one or more positioning appliances for realigning teeth. Placement of an appliance over the teeth can provide controlled forces in specific locations to gradually move the teeth into a new configuration. Repetition of this process with successive appliances in progressive configurations can move the teeth through a series of intermediate arrangements toward a final desired arrangement.

In some applications, one or more attachments can be used in conjunction with the one or more appliances. Attachments are secured to a patient's teeth and interact with a surface of the dental appliance to provide one or more functions. For example, an attachment can be used as an anchor to hold a portion of the dental appliance in place while other portions move one or more teeth. Attachments can also be used to provide a force to a tooth to move that tooth in a particular direction.

Treatment professionals have access to a number of standard attachment types and these current attachments have one surface that is used to impart a force to move one or more teeth based on interaction of the attachment's surface and a surface on the dental appliance. In some instances, a custom attachment can be created for a particular movement and/or a particular patient geometry. Such movements of teeth are typically associated with a movement prescribed in a treatment plan and are typically selected by a treatment professional based upon the treatment professional's experience with the type of attachment.

Once selected, the attachment is fixed to the patient's tooth. The attachment selected by the treatment professional may provide the force necessary for one particular stage of the treatment plan.

A different attachment would then need to be placed on the patient's tooth at a different stage of the treatment plan to provide a different force. This may result in errors in the placement of the attachments by the treatment professional, increased cost (e.g., in fabricating and using multiple attachments and time spent by the patient and treatment professional), and/or increased risk of damage to the tooth in removal of the multiple attachments. Such issues may also result in providing more, less, or different movement to achieve the desired result than was initially predicted by the treatment professional.

DETAILED DESCRIPTION

The present disclosure involves the use of attachments that are attached to a patient's teeth, to be used to hold a dental appliance onto the teeth of the patient wherein the appliance is utilized to move on or more teeth by applying force on the one or more teeth or other teeth of the patient. Use of the attachments can be used to impart a particular force on one or more teeth that can be more favorable to a treatment than an appliance without the use of an attachment. Attachment embodiments of the present disclosure each have multiple surfaces that can be used in the movement of one or more teeth and these surfaces can be selectively used individually or in combination to effectuate the movement of the teeth.

For example, in some embodiments, a single surface can be selected from an attachment having five possible surfaces that could be used. In some such embodiments, when a successive dental appliance is placed on the attachment, one or more other attachment surfaces can be used in addition to or instead of the one used previously. As discussed herein, when the surfaces are not used, they may be referred to as inactive and selection and use of a surface may be referred to as activating a surface and that surface is, then active.

In some embodiments, multiple surfaces may be used together to effectuate the movement of one or more teeth. For example, If a tooth is to be aided in erupting from the gingiva, two surfaces (e.g., on opposite sides of the attachment) can be used to provide a more balanced force on the tooth than a single attachment surface. Additionally, in such an embodiment, more force may be applied to one of the two surfaces thereby encouraging the tooth to rotate, for example, if the tooth was not erupting in the correct vertical orientation, it may be straightened through use of these attachment surfaces. In another example, multiple surfaces can be engaged by the appliance to rotate the tooth (e.g., also to straighten the tooth vertically, but without erupting the tooth).

A few of the benefits of using such embodiments include, being able to affix the attachment and then activate different surfaces of the attachment for different phases of a treatment plan rather than having to affix an attachment and then remove it and replace it potentially for each successive stage of the treatment plan, and being able to utilize multiple surfaces to accomplish complex movements that could not previously be accomplished, among other benefits.

In contrast to some previous approaches as discussed above, a number of embodiments of the present disclosure feature a dental positioning appliance (e.g., aligner) interfacing with a multi-faceted attachment structure having multiple surfaces that can be activated to interface with surfaces on the dental positioning appliance and the structure being designed to be attached to a tooth of patient in a treatment specific fashion. For example, the attachment structure can include a plurality of surfaces designed to apply a force to the tooth in a variety of orientations to provide a variety of engagement forces. As discussed above, the attachments of the present disclosure can be used with a series of dental appliances. In some such embodiments, one, several, or all of a series of appliances can be designed to interface with a subset of the plurality of surfaces of the attachment structure to provide one or more engagement forces that are specific to a respective stage of a treatment plan associated with each appliance.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure. As used herein, "a number of" a particular thing can refer to one or more of such things (e.g., a number of forces can refer to one or more forces).

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1, and a similar element may be referenced as 206 in FIG. 2. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

Figure 1:
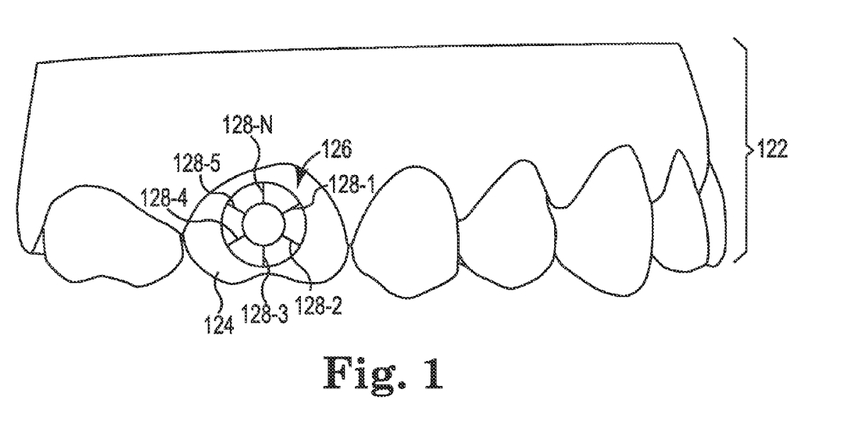
FIG. 1 illustrates an example view of a portion of a virtual model of a jaw including an attachment structure attached to a virtual tooth according to one or more embodiments of the present disclosure.

FIG. 1 illustrates an example view of a portion of a virtual model of a jaw 122 including an attachment structure 126 attached to a virtual tooth 124 according to one or more embodiments of the present disclosure. The virtual model of the jaw 122 can include a set of teeth of the jaw of the patient, including the virtual tooth 124. The attachment structure 126 can include a virtual model (e.g., a virtual attachment structure) of a physical attachment structure designed to be attached to at least one tooth of a patient.

Figure 2A:
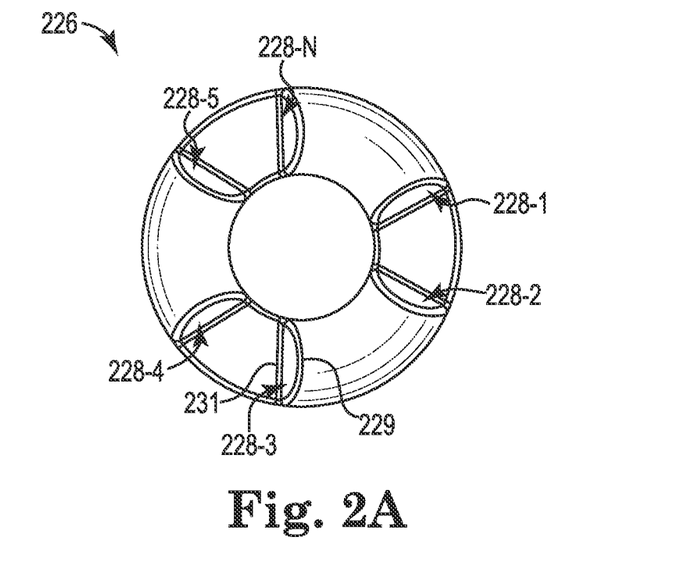
FIG. 2A illustrates an example of an attachment structure according to one or more embodiments of the present disclosure.

The attachment structure 126, as illustrated by FIG. 1, can include a geometric shape with a plurality of surfaces 128-1, 128-2, 128-3, 128-4, 128-5 . . . 128-N. The attachment structure 126 can be designed to be attached to a tooth of a patient (e.g., the tooth 124). The surfaces 128-1 . . . 128-N of the attachment structure, in some embodiments, can be formed by portions of the attachment structure 126 having a first height and portions of the attachment structure 126 having a second height, wherein the second height is greater than the first height (as illustrated in FIG. 2A). The surfaces 128-1 . . . 128-N can be the edges of the portions of the attachment structure 126 having the second height (e.g., the portions of the attachment structure 226 that are raised, also as illustrated in FIG. 2A).

However, embodiments in accordance with the present disclosure are not so limited. For example, in some embodiments, an attachment structure can include a plurality of attachment structure components (as discussed further herein with regard to FIG. 2B). In such embodiments, the surfaces of the attachment structure can include edges of each of the attachment structure components.

With respect to the example of FIG. 1, one or more appliances can be designed to interface with at least one surface of the attachment structure 126. For instance, an appliance can be designed to interface with a subset of the plurality of surfaces 128-1 . . . 128-N. The attachment structure 126 can be designed to be attached to the tooth 124 of the patient one time and subsequently be used to provide one or more engagement forces to the tooth 124 without removal or adjustment of the attachment structure. For instance, the surfaces 128-1 . . . 128-N of the attachment structure 126 can be oriented about the attachment structure 126 such that a variety of combinations of the surfaces 128-1 . . . 128-N can provide a variety of engagement forces.

Appliances according to the present disclosure can include, in some embodiments, a plurality of incremental dental position adjustment appliances. The appliances can be utilized to incrementally implement a treatment plan such as by affecting incremental repositioning of individual teeth in the jaw, among other suitable uses. In some implementations, appliances can be fabricated according to a virtual dental model that has had positions of a number of teeth adjusted according to one or more embodiments of the present disclosure.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance can, for example, be fabricated from a polymeric shell, and/or formed from other material, having a plurality of cavities therein. The cavities can be designed (e.g., shaped) to receive one or more teeth and/or apply force to reposition one or more teeth of a jaw from one teeth arrangement to a successive teeth arrangement. The shell may be designed to fit over a number of, or in many instances all, teeth present in the upper or lower jaw.

A cavity can be shaped to mate with a particular tooth. For example, a particular cavity can be shaped to mate with three surfaces of a corresponding tooth to be received therein. The cavity may be slightly out of alignment with a current configuration of the particular tooth (e.g., to facilitate aligning the particular tooth to a desired configuration), but the cavity can generally conform to the shape of the particular tooth such that there is not much space between the cavity and the particular tooth when the appliance is worn.

One or more of the surfaces of the attachment structure 126 can interface with a shell of an appliance to provide a particular engagement force. An engagement force, as used herein, can include a force on the tooth and/or interference between the one or more surfaces of the attachment structure 126 and the appliance (e.g., the shell) that produces a force when the appliance is worn by a patient. Example engagement forces can include one or more rotational forces, one or more linear forces, and/or one or more interferences with the appliance, among other forces.

The cavity shaped to mate with the tooth 124 that the attachment structure 126 is designed to be attached to can be slightly out of alignment with the current configuration of the particular tooth 124 to interface with the one or more surfaces of the attachment structure 126 and to provide the particular engagement force.

For example, an appliance can be designed to fit over teeth in a patient's jaw and the shell can be designed to interface with one or more surfaces of the attachment structure 126 and/or the teeth of the patient's jaw. The one or more surfaces that interface with the shell can be specific to a stage of a treatment plan for which the appliance was designed. For example, successive appliances created according to a treatment plan may include a shape designed to interface with more activated surfaces 128-1 . . . 128-N. The one or more surfaces can be activated, as discussed further herein, according to a model of a number of forces used to reposition the at least one virtual tooth 124 a distance according to a stage of the treatment plan. For instance, an activated surface of an attachment structure, as used herein, is applying a force and a surface of the attachment structure that is not activated is not applying a force. Surfaces are activated when a designer of an appliance selects a surface of the attachment structure to interface with a surface on the appliance to provide a force (e.g., an engagement force).

An appliance that includes a shape designed to interface with an activated surface of an attachment structure, as used herein, can include a physical appliance with a shape that interfaces with the activated surface of the attachment structure when the physical appliance is worn by a patient. The shape designed to interface with an active surface can include a portion of the appliance, such as a portion of a cavity. Example shapes can include a shape of the cavity and/or a portion of the cavity that is slightly out of alignment with the current configuration of the particular tooth and designed to interface with the activated surface of the attachment structure. The shape interfacing with the activated surface can provide the engagement force (e.g., force on the tooth and/or interference between the surface and the appliance that produces a force).

The one or more surfaces that interface with the appliance can include a subset of the plurality of surfaces 128-1 . . . 128-N (i.e., less than all of the surfaces that could be used to interface with an appliance) activated to interface with an appliance of a particular stage of a treatment plan to provide an engagement force to the one or more teeth that is specific to a particular stage of the treatment plan. For instance, a treatment plan can include a series of appliances designed to incrementally implement the treatment plan.

A first appliance of the series can comprise a first shell having a plurality of cavities therein designed to receive teeth of a jaw of the patient. The first shell can be designed to interface with a first surface or a first subset of the plurality of surfaces 128-1 . . . 128-N of the attachment structure 126 to provide a first engagement force (in the case of a first subset, the first engagement force will be a combination of forces of the subset of surfaces at a selected time in the stage of the treatment plan) specific to a first stage of the treatment plan.

The first surface or a first subset of the surfaces 128-1 . . . 128-N can be activated (e.g., selected to interface with the shell of the particular stage of the treatment plan), for instance, based on a model of a number of forces used to reposition at least one virtual tooth 124 a first distance according to the first stage of the treatment plan (e.g., as discussed further herein). For instance, the first shell can be designed to interface with the first surface or the first subset of surfaces 128-1 . . . 128-N to provide the first engagement force to move the at least one tooth 124 toward a first position that is specific to the first stage of the treatment plan. Alternatively, the first shell can be designed to interface with the first surface or the first subset of surfaces 128-1 . . . 128-N to provide the first engagement force to prevent and/or minimize movement of and/or forces on the at least one tooth 124.

A second appliance of the series can comprise a second shell having a plurality of cavities therein designed to receive teeth of a jaw of the patient. The second shell can be designed to interface with a second surface or a second subset of the plurality of surfaces 128-1 . . . 128-N of the attachment structure 126 to provide a second engagement force specific to a second stage of the treatment plan.

The second surface or second subset of the surfaces 128-1 . . . 128-N can be activated, for instance, based on a model of a number of forces used to reposition the at least one virtual tooth 124 a second distance according to the second stage of the treatment plan (e.g., as discussed further herein). For instance, the second shell can be designed to interface with the second surface or the second subset of the surfaces 128-1 . . . 128-N to provide the second engagement force to move the at least one tooth 124 toward a second position that is specific to the second stage of the treatment plan.

Alternatively, the second shell can be designed to interface with the second surface or the second subset of surfaces 128-1 . . . 128-N to provide the second engagement force to prevent and/or minimize movement of and/or forces on the at least one tooth 124. The first engagement force and the second engagement force can include different forces (e.g., forces specific to the respective stage of the treatment plan).

The first subset and the second subset can, for instance, include at least one surface that is different between them. That is, the subsets can include different combinations of the plurality of surfaces 128-1 . . . 128-N. In some embodiments, the first subset and the second subset can include at least one common surface between them.

As used herein, a "first stage" does not necessarily mean the original stage of a treatment plan, but is a relative term with respect to other stages. For example, the "first stage" may be a second stage of a 25 stage treatment plan, while the "second stage" may be a tenth stage of the 25 stage treatment plan, with the "third stage", for example, being a 15th stage of the 25 stage treatment plan, and the "fourth stage" may be a 24th stage of the 25 stage treatment plan.

As discussed above, a single attachment structure 126 with a plurality of surfaces 128-1 . . . 128-N, that can be individually activated in a variety of combinations to provide a variety of engagement forces specific to particular stages of treatment, can be advantageous over some previous approaches that include different attachments for different treatment stages and therefore may require that a treatment professional attach and/or remove attachments at various stages of the treatment plan. Such additional attachments and/or removal procedures can lead to additional visits to a treatment professional, increased error in attachment by the treatment professional, lengthening a treatment plan duration, a need for a revised treatment plan, and/or unnecessary patient discomfort, among other drawbacks.

In contrast, a number of embodiments of the present disclosure allow for more timely, efficient, accurate, and/or comfortable execution of treatment plans. For instance, the single attachment structure can be attached to a tooth 124 of the patient and the plurality of surfaces 128-1 . . . 128-N can be designed to apply a force thereto in a variety of orientations to provide a variety of engagement forces.

Although not specifically illustrated, in some embodiments, for a particular stage in a treatment plan, both an upper appliance (an appliance designed to fit over teeth of a patient's upper jaw) and lower appliance (an appliance designed to fit over teeth of a patient's lower jaw) can be designed to interface with an attachment structure embodiment of the present disclosure (i.e., attachments fixed to teeth on the upper jaw and other attachments fixed to teeth on the lower jaw). A particular stage in a treatment plan can include attachment structures on only one of an upper appliance and a lower appliance.

Another particular stage in a treatment plan may not include any attachment structures on either an upper appliance or a lower appliance. And, another particular stage in a treatment plan can include attachment structures on cavities corresponding to incisors, canines, premolars, and/or molars, and/or any combination thereof.

For instance, the first appliance and second appliance can be designed to receive teeth of a first jaw (e.g., an upper jaw) and interface with a first attachment structure. A third appliance of the set of appliances can comprise a third shell having a plurality of cavities therein designed to received teeth of a second jaw (e.g., a lower jaw) of the patient during a first stage of the treatment plan.

A second attachment structure designed to be attached to at least one tooth of the second jaw can include a plurality of surfaces. The third shell can be designed to interface with a first surface or a first subset of surfaces of the plurality of surfaces of the second attachment structure to provide a third engagement force specific to the first stage of the treatment plan.

A number of embodiments of the present disclosure include instructions that are executable by a processor (e.g., software), which can be fixed in a non-transitory computing device readable medium, to model a patient's jaws (e.g., including teeth, roots, gingiva, and/or supporting structure, etc.). The instructions can be executed to create and/or modify a treatment plan to incrementally adjust the patient's teeth and/or bite, among other adjustments, via application of a series of appliances as described herein. The instructions can be executed to provide modified models of the patient's jaws 122 for each of the various stages of the treatment plan for fabrication (e.g., via rapid prototyping such as stereolithography) of physical models corresponding to the virtual models. The physical models can be used for the fabrication (e.g., via thermoforming) of appliances thereover.

According to a number of embodiments of the present disclosure, the instructions can be executed to position an attachment structure 126 on a corresponding one or more virtual teeth 124 of a virtual model of a jaw 122. The instructions can be executed to activate a first subset of a plurality of surfaces 128-1 . . . 128-N of the attachment structure 126 to provide an engagement force at a particular stage of treatment and/or activate different subsets of surfaces 128-1 . . . 128-N of the attachment structure 126 for subsequent stages of treatment.

As discussed above, activating a surface of an attachment structure, as used herein, can include selecting the surface to interface with a shell of a particular stage of the treatment plan. The virtual model of the jaw 122 can be different at each stage of treatment according to the treatment plan (e.g., positioning of the virtual teeth can change) and therefore the surfaces that are activated can change from one stage of treatment to another. The instructions can be executed to change the activated surfaces of the attachment structure 126 according to changes to the virtual model of the jaw 122 between treatment stages and/or according to anticipated changes in subsequent stages of treatment (e.g., to help effectuate a desired movement of one or more virtual teeth of the virtual model of the jaw 122).

For each stage of treatment, the instructions can be executed to model engagement forces applied to the virtual model of the jaw 122 by an appliance corresponding to that stage (to simulate actual forces to be applied to a patient's physical jaw by a physical appliance and the physical appliance interfacing with an attachment structure 126/to simulate actual interference of the surfaces of the attachment structure 126 with the physical appliance that produces a force). Those forces can include forces applied to the virtual model of the jaw 122 by virtue of the appliance being slightly out of alignment with a current configuration of the virtual teeth and/or include inherent forces applied to the aligner by the patient (e.g., when the shell of the appliance interfaces with one or more surfaces of the attachment structure 126).

The virtual models illustrated and/or described herein (e.g., FIG. 1, etc.) can represent a stage of a treatment plan, can be used to model forces applied to the virtual models, can be used to create a physical model for formation of a physical appliance thereover, and/or can be used for direct fabrication of a physical appliance (without creating a physical model), among other uses.

Positioning an attachment structure 126 and/or activating one or more surfaces 128-1 . . . 128-N to interface with a shell on a virtual model of a jaw 122 can be automatic (e.g., by operation of software based on force modeling for a particular stage of treatment), manual (e.g., by operation of an operator interacting with the virtual model via an interface with a computing device), or a combination thereof. Likewise, the shape (e.g., size, orientation (e.g., various angles with respect to references)) and/or attachment location (on the virtual tooth 124) of the attachment structure 126 can be automatically set by the software, by manual operation (e.g., an operator can specify the necessary criteria of the virtual attachment structure and/or modify default criteria provided by the software), or a combination thereof.

The instructions to position the attachment structure 126 and/or activate one or more surfaces 128-1 . . . 128-N can incorporate a result of instructions to model forces used to reposition virtual teeth. For example, the instructions can be executed to model a first number of forces used to reposition a corresponding at least one virtual tooth a first distance according to a first stage ("first" indicating an arbitrary stage, not necessarily an original stage) of a treatment plan and the instructions can be executed to incorporate a result of modeling the first number of forces in order to position the attachment structure 126 and/or activate a first subset of the plurality of surfaces 128-1 . . . 128-N to interface with a first shell to provide a first engagement force corresponding to a first stage of the treatment plan. The instructions executed to activate a second subset of the surfaces 128-1 . . . 128-N can incorporate a result of instructions executed to model a second number of forces used to reposition the at least one virtual tooth a second distance according to a second stage of the treatment plan (e.g., a stage subsequent to the first stage, but not necessarily sequential thereto).

According to a number of embodiments of the present disclosure, the activated one or more surfaces 128-1 . . . 128-N can be specific to a particular stage of treatment. The activated surfaces 128-1 . . . 128-N for subsequent stages of treatment can change from the activated surfaces for the particular stage based on the particular forces to move the one or more teeth in the subsequent stages (e.g., to help effectuate a desired change to the virtual model of the jaw 122).

More accurate modeling of the force applied by the one or more surfaces 128-1 . . . 128-N of the attachment structure 126 interfacing with the shell of the dental appliance can lead to more favorable results from the treatment plan for the patient (e.g., the actual results can more accurately reflect the modeled results in the treatment plan).

Various stages of a treatment plan can include or not include an appliance to cover the teeth of the opposing jaw and different stages of the treatment plan can include or not include activated surfaces 128-1 . . . 128-N of the attachment structure 126. For example, a particular stage of a treatment plan can include an appliance over each of the upper jaw and lower jaw of a patient, where one of the appliances includes shapes designed to interface with the activated surfaces 128-1 . . . 128-N of the attachment structure 126, and where the attachment structure 126 is designed to interface with the particular appliance to provide an engagement force specific to a stage of the treatment plan.

A number of appliances in a series of appliances created as part of a treatment plan can perform different functions. Some of the functions performed by different appliances in the series may overlap and some may be unique to a particular appliance. By way of example, a first appliance can interface with a first subset of surfaces 128-1 . . . 128-N of an attachment structure 126 designed to provide a first engagement force to a tooth 124 of a first jaw and/or a second jaw to move the tooth 124 a first distance specific to a first stage of the treatment plan. A second appliance can interface with a second subset of surfaces 128-1 . . . 128-N of the attachment structure 126 designed to provide a second engagement force to the tooth 124 of a first jaw and/or a second jaw to move the tooth 124 a second distance specific to a second stage of the treatment plan. A third appliance may, for instance, minimize (e.g., avoid) and/or not interface with surfaces 128-1 . . . 128-N of the attachment structure 126.

FIG. 2A illustrates an example of an attachment structure 226 according to one or more embodiments of the present disclosure. The attachment structure 226 can include a body structure designed to be attached to at least one tooth of a jaw of a patient and a plurality of surfaces 228-1, 228-2, 228-3, 228-4, 228-5 . . . 228-N (herein generally referred to as "the surfaces 228"). The body structure, in some embodiments, can include a geometric shape. Example geometric shapes can include a circle, oval, rectangle, hexagon, etc.

The surfaces 228 can be oriented about the body structure. For instance, the surfaces 228 can be oriented normal to one another about the body structure and designed to be separately activated in a variety of orientations (e.g., to provide a variety of engagement forces). Normal to one another, as used herein, can include a surface that is perpendicular to a tangent vector of the curve of the attachment structure 226. The surfaces 228 can include, for instance, at least three surfaces. In various embodiments, as illustrated by FIG. 2A, the surfaces 228 can include six surfaces. Although embodiments in accordance with the present disclosure are not so limited and can include variety of number of surfaces.

The surfaces 228, as illustrated by the embodiment of FIG. 2A, can be formed by portions of the attachment structure 226 having a first height 231 and portions of the attachment structure 226 having a second height 229, wherein the second height 229 is greater than the first height 231. That is, portions of the attachment structure 226 can have a greater height than other portions. The surfaces 228 can be the edges of the portions of the attachment structure 226 having the second height 229 (e.g., the edges of the portions of the attachment structure that are raised).

In some embodiments, the edges can be perpendicular to one or both of the portions of the attachment structure having a first height 231 and second height 229. In some embodiments, the angle of the edge can be greater or less than perpendicular.

For example, one attachment structure embodiment can include a body structure designed to be attached to at least one tooth of a jaw, at least three surfaces about the body structure, wherein the at least three surfaces are oriented normal to one another about the body structure and designed to be separately selected in a variety of orientations, and wherein the attachment structure is designed to interface with a first appliance of a series of appliances designed to incrementally implement a treatment plan to provide a first engagement force specific to a first stage of the treatment plan and designed to interface with a second appliance of the series to provide a second engagement force specific to a second stage of the treatment plan, and wherein the first engagement force and the second engagement force include different forces.

Figure 2B:
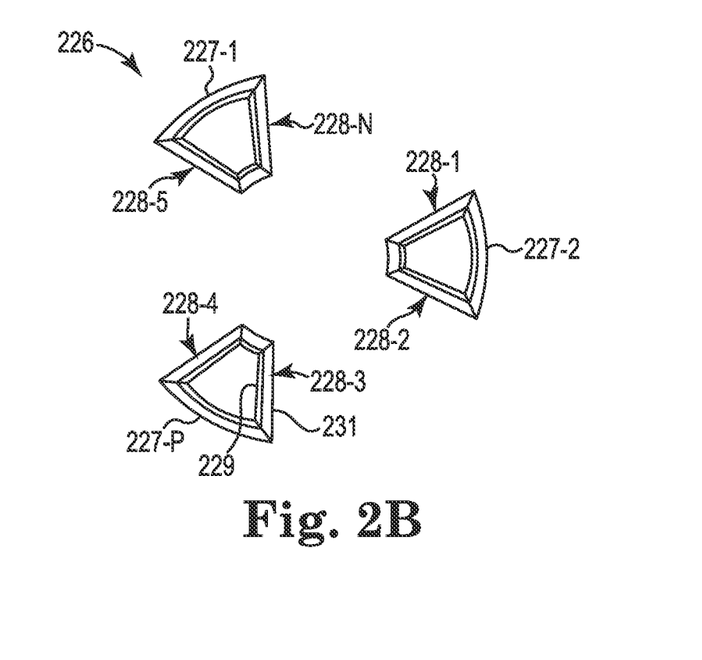
FIG. 2B illustrates an example of a plurality of attachment structure components according to one or more embodiments of the present disclosure.

FIG. 2B illustrates an example of a plurality of attachment structure components 227-1, 227-2 . . . 227-P according to one or more embodiments of the present disclosure. In some embodiments, the attachment structure 226, as illustrated in the embodiment of FIG. 2B, can include a plurality of attachment structure components 227-1, 227-2 . . . 227-P (herein generally referred to as "the attachment structure components 227") each individually designed to be attached to at least one tooth of a jaw of a patient.

The attachment structure 226 can include a plurality of surfaces 228-1, 228-2, 228-3, 228-4, 228-5 . . . 228-N (herein generally referred to as "the surfaces 228"). Each of the attachment structure components 227 can, for example, include one or more of the surfaces 228. For instance, the surfaces 228 can be oriented normal to one another about the geometric shape formed by the plurality of attachment structure components 227. The surfaces 228 can include, for instance, at least three surfaces. In various embodiments, as illustrated by FIG. 2A, the surfaces 228 can include six surfaces. In such embodiments, the surfaces 228 of the attachment structure 226 can include the edges of each of the attachment structure components 227.

Each of the plurality of attachment structure components 227, as illustrated by the embodiment of FIG. 2B, include a first height 231 and a second height 229, wherein the second height 229 is greater than the first height 231. The surfaces 228 can be the edges of the portions of the attachment structure components 227 having the second height 229 (e.g., the edges of the portions of the attachment structure that are raised).

Figure 2C:
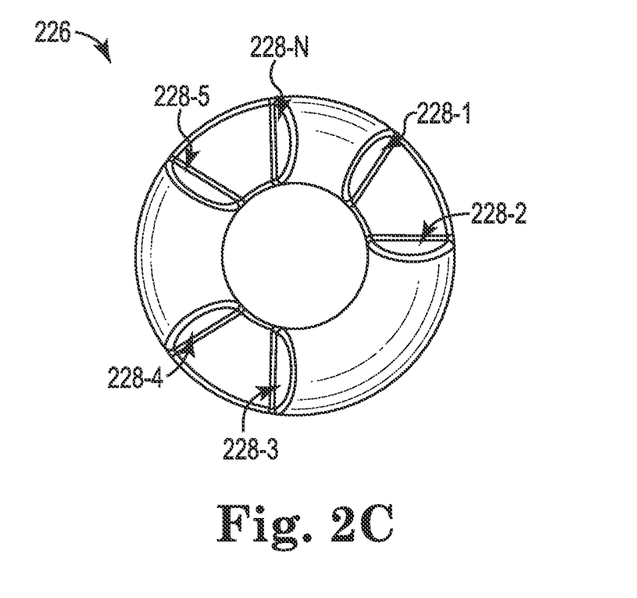
FIG. 2C illustrates an example of an attachment structure according to one or more embodiments of the present disclosure.

FIG. 2C illustrates an example of an attachment structure 226 according to one or more embodiments of the present disclosure. As discussed above, the attachment structure 226 can include a body structure designed to be attached to at least one tooth of a jaw of a patient and a plurality of surfaces 228-1, 228-2, 228-3, 228-4, 228-5 . . . 228-N (herein generally referred to as "the surfaces 228").

As illustrated by the embodiment of FIG. 2C, in various examples, the surfaces 228 can be oriented about the body structure at a variety of distances. That is, the distance of portions of the attachment structure 226 at a first height and a second height can also be varying distances.

Figure 3:
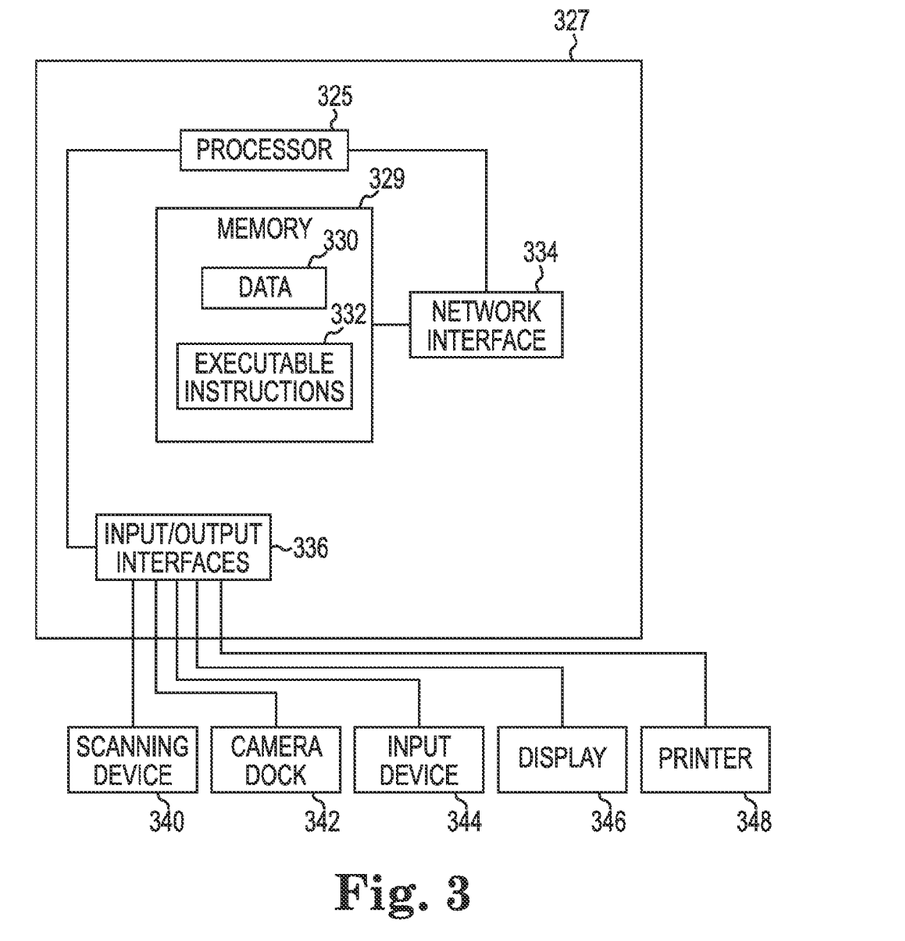
FIG. 3 illustrates a system for treatment planning according to one or more embodiments of the present disclosure.

FIG. 3 illustrates a system for treatment planning according to one or more embodiments of the present disclosure. In the system illustrated in FIG. 3, the system includes a computing device 327 having a number of components coupled thereto. The computing device 327 includes a processor 325 and memory 329. The memory 329 can include various types of information including data 330 and executable instructions 332 as discussed herein.

Memory and/or the processor may be located on the computing device 327 or off the device in some embodiments. As such, as illustrated in the embodiment of FIG. 3, a system can include a network interface 334. Such an interface can allow for processing on another networked computing device or such devices can be used to obtain information about the patient or executable instructions for use with various embodiments provided herein.

As illustrated in the embodiment of FIG. 3, a system can include one or more input and/or output interfaces 336. Such interfaces can be used to connect the computing device with one or more input or output devices.

For example, in the embodiment illustrated in FIG. 3, the system includes connectivity to a scanning device 340, a camera dock 342, an input device 344 (e.g., a keyboard, mouse, etc.), a display device 346 (e.g., a monitor), and a printer 348. The processor 325 can be configured to provide a visual indication of a virtual model on the display 346 (e.g., on a GUI running on the processor 325 and visible on the display 346). The input/output interface 336 can receive data, storable in the data storage device (e.g., memory 328), representing the virtual model (e.g., corresponding to the patient's upper jaw and the patient's lower jaw).

In some embodiments, the scanning device 340 can be configured to scan a physical mold of a patient's upper jaw and a physical mold of a patient's lower jaw. In one or more embodiments, the scanning device 340 can be configured to scan the patient's upper and/or lower jaws directly (e.g., intraorally).

The camera dock 342 can receive an input from an imaging device (e.g., a 2D imaging device) such as a digital camera or a printed photograph scanner. The input from the imaging device can be stored in the memory 329.

Such connectivity can allow for the input and/or output of virtual model information or instructions (e.g., input via keyboard) among other types of information. Although some embodiments may be distributed among various computing devices within one or more networks, such systems as illustrated in FIG. 3 can be beneficial in allowing for the capture, calculation, and/or analysis of information discussed herein.

The processor 325, in association with the memory 329, can be associated with data and/or application modules. The processor 325, in association with the memory 329, can store and/or utilize data and/or execute instructions to provide treatment planning that includes an attachment structure.

Such data can include the virtual model described herein (e.g., including a first jaw, a second jaw, a number of appliances, etc.). Such executable instructions can include instructions for attachment structure design and/or placement, force calculation, engagement force calculation, and/or treatment planning, among other functions.

Instructions for attachment structure design and/or placement can be configured to position an attachment structure on at least one virtual tooth of a virtual model of a jaw. The attachment structure instructions can be configured to incorporate a result of a number of forces modeled by the force calculation instructions (e.g., forces used to reposition the corresponding at least one virtual tooth a first distance according to a first stage of the treatment plan).

For example, in response to a determination that at least one of the number of forces used to reposition the corresponding at least one virtual tooth the first distance is greater than a force a physical appliance can physically apply to the physical tooth, an attachment structure can be positioned on the at least one virtual tooth. As an example, the amount of surface area of the tooth perpendicular to a line of movement (e.g., a vector to move the tooth the first distance) may be insufficient for the appliance to deliver the necessary force.

Alternatively and/or in addition, one of the number of forces (and/or one of the engagement forces calculated, as discussed further herein) can include and/or cause an undesirable or unwanted force on the at least one virtual tooth. Such a force can include, for instance, a force beyond a threshold force and/or a force that tips a tooth beyond a threshold, among other forces.

The attachment structure instructions can be configured to activate a first subset of the plurality of surfaces of the attachment structure at a first stage of a treatment plan that is incremented in stages. For instance, the attachment structure instructions can be configured to incorporate a result of instructions to model a first number of forces used to reposition the corresponding at least one virtual tooth a first distance according to the first stage of the treatment plan to activate the first subset of the plurality of surfaces.

The attachment structure instructions can be configured to activate a second subset of the plurality of surfaces of the attachment structure at a second stage of the treatment plan according to changes to the virtual model of the jaw between the first stage of the treatment plan and the second stage of the treatment plan. For example, the attachment structure instructions can be configured to incorporate a result of instructions to model a second number of forces used to reposition the corresponding at least one virtual tooth a second distance according to the second stage of the treatment plan (e.g., forces used to reposition the corresponding virtual tooth a second distance according to a second stage of the treatment plan).

Activating a surface, as previously discussed, can include selecting the surface to interface with a shell corresponding to a particular stage of the treatment plan. For instance, activating a surface can include changing a characteristic of the virtual model of the attachment structure.

As an example, an initial virtual attachment structure attached to the tooth can include the attachment structure and/or a plurality of attachment structure components that have a first height (e.g., as illustrated by the attachment structure 126 of FIG. 1, wherein the portions of the attachment structure are a first height/flat). In response to determining to activate a surface, a portion of the virtual attachment structure can be changed to a second height.

The first height can include a lower height than the second height. Thereby, changing the portion of the virtual attachment structure to a second height can create the virtual activated surface. The shape of the cavity of the shell (e.g., virtual model of the shell and/or the physical device to be formed from the virtual model) designed to interface with the activated surface can, for instance, be slightly out of alignment with the current configuration of the particular tooth to interface with the one or more surfaces of the attachment structure and to provide the particular engagement force.

Alternatively, an initial virtual attachment structure can have portions of a first height and portions of a second height (e.g., as illustrated by the attachment structures 226 illustrated in FIGS. 2A-2B). In response to determining to activate a surface, a portion of the attachment structure of the second height proximal to the activated surface can have a length changed from a first length to a second length proximal to the activated surface.

The second length can include a smaller length than the first length. A length of a portion of the attachment structure, as used herein, can include a distance about the attachment structure. Thereby, the length of the portion of the virtual attachment structure (and/or a physical mold) can include a smaller length than the physical length of the portion of the physical attachment structure designed to be attached to a tooth. The shape of the cavity of the shell (e.g., virtual model of the shell and/or the physical device to be formed from the virtual model) designed to interface with the activated surface can, for instance, include additional material designed to interface with the one or more surfaces of the attachment structure and to provide the particular engagement force.

The force calculation instructions can be configured to model one or more forces used to reposition one or more teeth a distance according to a treatment plan. For instance, the force calculation instructions can model a first number of forces used to reposition at least one virtual tooth a first distance according to a first stage of the treatment plan and a second number of forces used to reposition at least one virtual tooth a second distance according to a second stage of the treatment plan. The treatment plan instructions can be configured to create, edit, delete, revise, or otherwise modify the treatment plan (e.g., based at least in part on operation of other application instructions).

The engagement force instructions can be configured to model engagement forces to be applied to one or more teeth of a patient by wearing a corresponding appliance (e.g., with shape designed to interface with the activated surfaces of the respective stage of the treatment plan). Modeling an engagement force can include, for example, modeling an interference between the activated surfaces and the appliance that produces a force. For example, the engagement force instructions can model a first engagement force to be applied by a first subset of the plurality of surfaces of the attachment structure interfacing with a corresponding one of the appliances during the first stage of the treatment plan and model a second engagement force to be applied by a second subset of the plurality of surfaces of the attachment structure interfacing with a corresponding one of the appliances during the second stage of the treatment plan.

In some embodiments, the attachment structure instructions and/or the treatment plan instructions can revise a shape, location, and/or orientation of the attachment structure based on at least one of the modeled first engagement force and the modeled second engagement force. For instance, the modeled engagement forces may identify a force on a tooth and/or an appliance that is above a threshold, inadequate to move the tooth the particular distance, and/or includes an unwanted and/or undesirable force, among other forces.

In various embodiments, a generalized engagement force can be modeled based on testing in a lab. For example, during development of the attachment structure, a physical mold of teeth can be used to test generalized engagement forces applied by a physical attachment structure interfacing with a physical appliance. Attachment structures, positioning of the attachment structures, and/or activated surfaces can be revised and physically tested to determine a number of generalized engagement forces. The generalized engagement forces can be input as attachment structure instructions and/or the treatment plan instructions to assist in modeling engagement forces to be applied by the attachment structure and the activated surfaces interfacing for a number of patients when a treatment is applied.

The virtual model can be provided (e.g., via network interface 334) for fabrication of physical models corresponding to the jaw at the first and the second stages of the treatment plan for formation of appliances thereover such that the appliances includes a shape designed to interface with the activated surfaces of the attachment structure. For instance, an appliance that includes the shape designed to interface with the activated surfaces can include a surface on the shell of the appliance designed to interface with the activated surfaces (e.g., a lip similar to that discussed with respect to FIG. 1).

Figure 4:
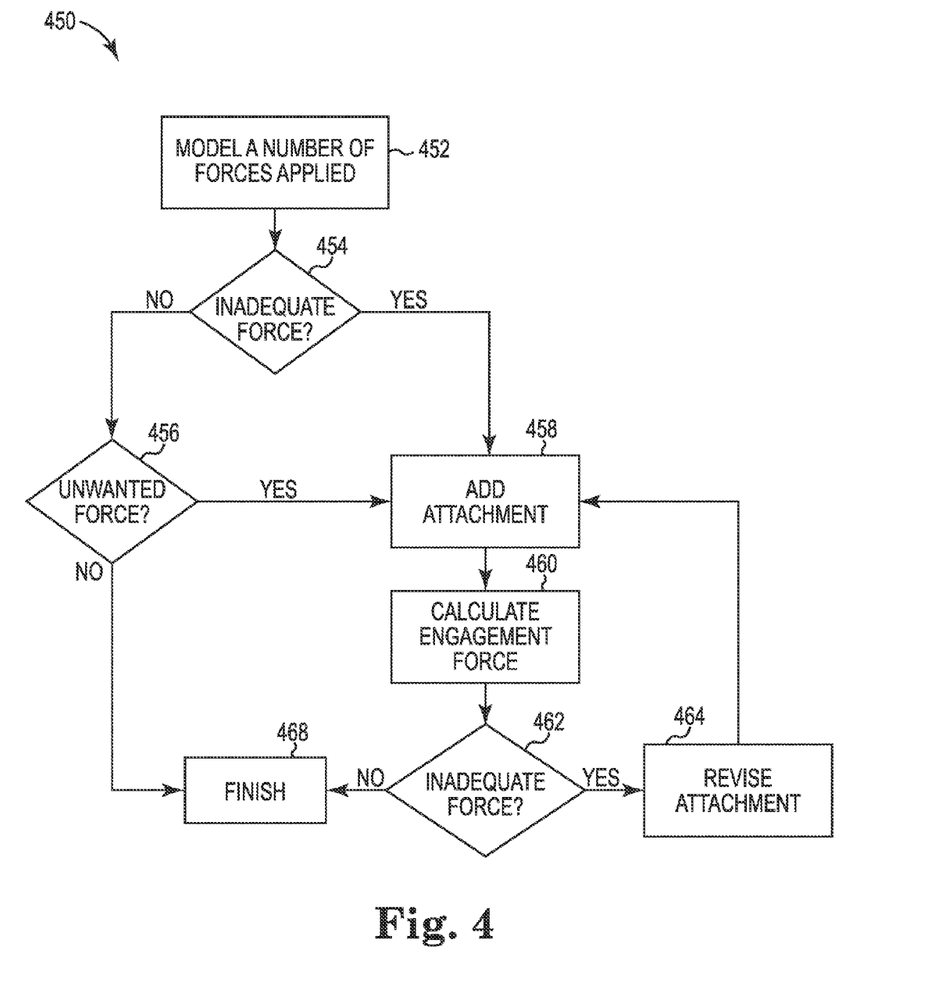
FIG. 4 illustrates an example process for treatment planning according to one or more embodiments of the present disclosure.

FIG. 4 illustrates an example process 450 for treatment planning according to one or more embodiments of the present disclosure. At block 452, the process 450 can include modeling a number of forces to apply to move one or more teeth a distance specific to a stage of a treatment plan. At block 454, a determination is made whether a physical appliance can apply the number of forces.

In response to determining the appliance is able to apply the number of forces, at block 456, a determination is made as to whether the number of forces include an unwanted and/or undesirable force. In response to determining the number of forces do not include an unwanted and/or undesirable force, the process can be complete at block 468 (e.g., a virtual model of the appliance, virtual model of a jaw, a physical model of the jaw, and/or a physical appliance can be created). As used herein, a virtual model is a computing device generated version of a physical dental appliance and/or attachment that can be viewed by a computing device display and/or be used to fabricate a physical dental appliance and/or attachment.

In response to determining that the appliance is unable to apply at least one of the number of modeled forces (e.g., from block 454) and/or determining the number of forces include an unwanted and/or undesirable force (e.g., from block 456), the process 450, at block 458, can include adding an attachment structure to a virtual model of one or more teeth. The attachment structure can include a plurality of surfaces.

One or more of the surfaces can be activated based on the number of modeled forces. For instance, the one or more surfaces can be activated to allow the appliance to apply the number of forces, and/or to prevent and/or minimize an unwanted and/or undesirable force.

At block 460, an engagement force to be applied by the one or more activated surfaces of the attachment structure interfacing with a corresponding appliance during a stage of the treatment plan can be calculated (e.g., modeled). The corresponding appliance can include a shape designed to interface with the activated surfaces. Thereby, the calculated engagement force can include a number of forces applied to the one or more virtual teeth of the patient and/or the appliance (e.g., an interference) when the appliance and the attachment structure interface.

At block 462, a determination can be made whether the engagement force is adequate. For instance, the engagement force can be compared to the modeled number of forces to apply to move one or more teeth a distance specific to a stage of a treatment plan.

In response to identifying the engagement force is above a threshold force (e.g., above a maximum force to apply to a tooth and/or an appliance), insufficient to move the one or more teeth the distance (e.g., is less than one or more of the number of forces), and/or includes an unwanted and/or undesirable force, at block 464, the attachment structure can be revised. For instance, revising the attachment structure can include revising activated surfaces, a shape, a location, and/or an orientation on the structure and/or changing the instructions provided to the treatment professional regarding the positioning of the attachment on the tooth (move the attachment up or down on the tooth and/or rotate the attachment to change the angle of the surfaces with respect to the appliance), among other revisions, of the attachment structure.

The revised attachment structure can be added to the one or more virtual teeth (e.g., block 458), a new engagement force can be calculate (e.g., at block 460), the new engagement force calculated can be compared to the modeled number of forces, a threshold force, and/or unwanted and/or undesirable forces (e.g., at block 462) and such adjustments can be iteratively done until a most suitable implementation is identified, by a treatment professional and/or a computing device, for example, through comparison of the force analyses done in these iterations. In response to identifying that the engagement force (and/or new engagement force) is an adequate force, at block 468, the process 450 can finish.

Figure 5A:
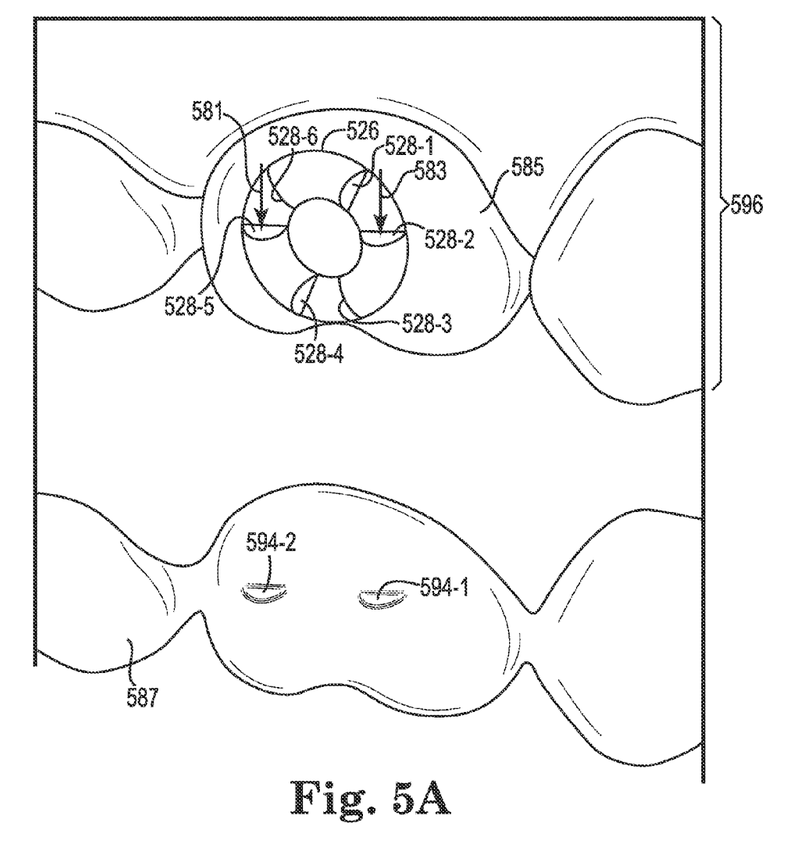
FIG. 5A-5C illustrate examples of a jaw include an attachment structure attached to a tooth and a series of appliances according to one or more embodiments of the present disclosure.
Figure 5B:
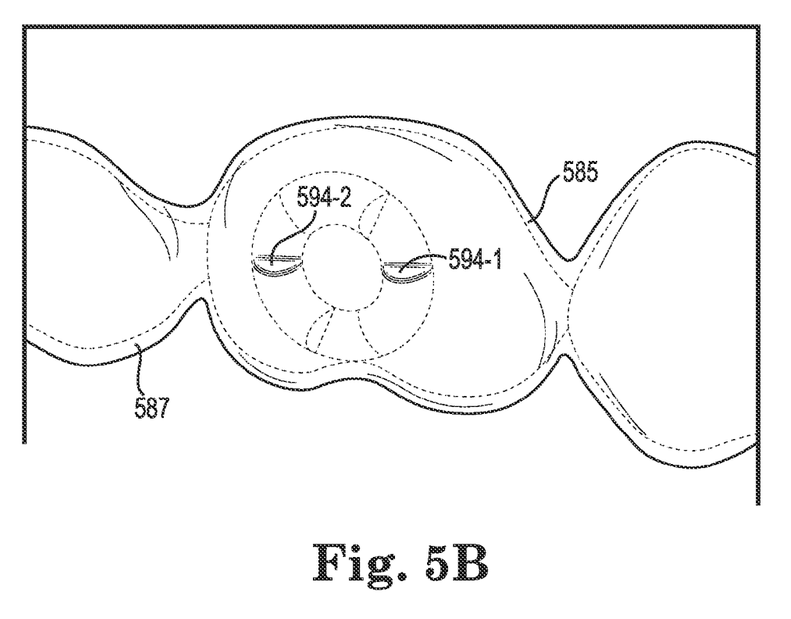
Figure 5C:
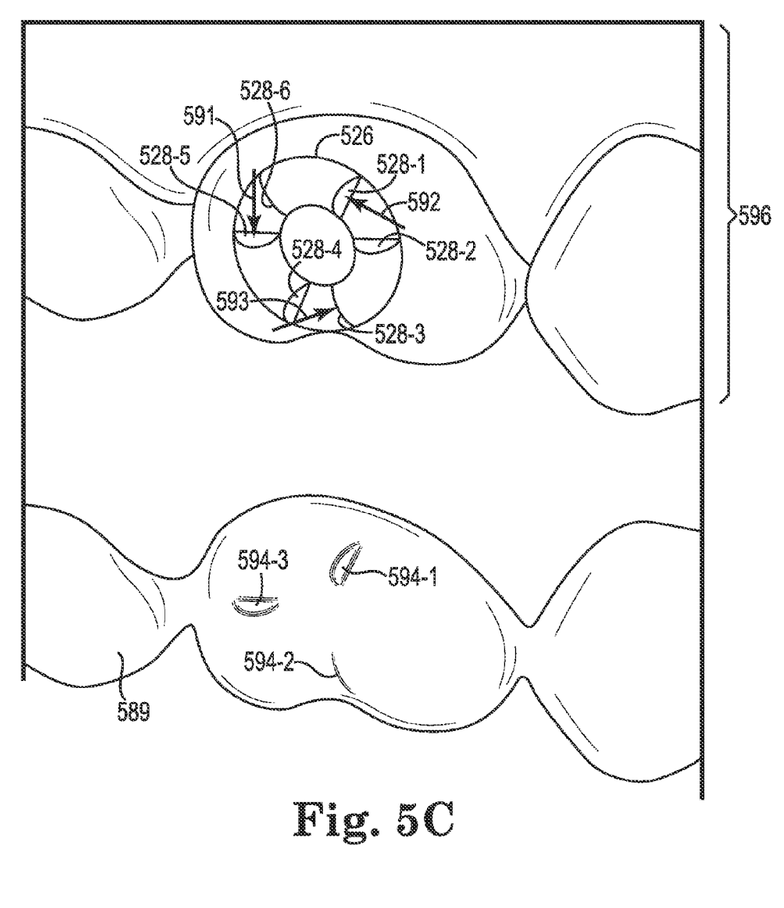

FIG. 5A-5C illustrate examples of a jaw 596 including an attachment structure 526 attached to a tooth 585 and a series of appliances 587,589 according to one or more embodiments of the present disclosure. The jaw 596 can include a physical jaw and/or a virtual model of a jaw. For instance, the jaw 596 can include a set of teeth of the jaw of the patient, including the tooth 585. The attachment structure 526 can include a virtual model (e.g., a virtual attachment structure) of a physical attachment structure and/or a physical attachment structure.

The attachment structure 526, as illustrated by FIGS. 5A-5C, can include a geometric shape with a plurality of surfaces 528-1, 528-2, 528-3, 528-4, 528-5, 528-6. The attachment structure 526 can be designed to be attached to a tooth 585 of a patient. Alternatively, in some embodiments, an attachment structure can include a plurality of attachment structure components (as illustrated by FIG. 2B).

With respect to the example of FIGS. 5A-5C, one or more appliances 587, 589 can be designed to interface with at least one surface of the attachment structure 526. For instance, an appliance can be designed to interface with a subset of the plurality of surfaces 528-1 . . . 528-6. The attachment structure 526 can be designed to be attached to the tooth 585 of the patient at one stage of the treatment plan and subsequently used at another stage of the treatment plan to provide one or more engagement forces to the tooth 585 without removal or adjustment of the attachment structure 526. For example, the surfaces 528-1 . . . 528-6 of the attachment structure 526 can be oriented about the attachment structure 526 such that a variety of combinations of the surfaces 528-1 . . . 528-6 can provide a variety of engagement forces.

The appliances 587, 589 illustrated by FIGS. 5A-5C can include and/or be part of a series of appliances. A series of appliances according to the present disclosure can include a plurality of incremental dental position adjustment appliances. The appliances can be utilized to incrementally implement a treatment plan such as by affecting incremental repositioning of individual teeth in the jaw, among other suitable uses.

For example, FIGS. 5A-5B illustrate a first appliance 587 of a series of appliances. A first appliance 587 of the series can be designed to fit over teeth in a jaw of a patient and can comprise a first shell having a plurality of cavities designed to receive teeth of the jaw of the patient. The first shell can be designed to interface with one or more surfaces of the attachment structure 526 and/or the teeth of the patient's jaw. The one or more surfaces that interface with the first shell can be specific to a stage of a treatment plan for which the first appliance 587 was designed.

For example, successive appliances created according to a treatment plan may include a shape designed to interface with one or more activated surfaces 528-1 . . . 528-6. The one or more surfaces can be activated, as previously discussed herein, according to a model of a number of forces used to reposition the at least one tooth 585 a distance according to a stage of the treatment plan.

FIG. 5C includes an illustration of a second appliance 589 of the series. A second appliance 589 of the series can comprise a second shell having a plurality of cavities therein designed to receive teeth of the jaw of the patient (e.g., the same jaw that the first appliance 587 illustrated by FIG. 5A-5B is designed to receive). The second shell can be designed to interface with a second surface or a second subset of the plurality of surfaces 528-1 . . . 528-6 of the attachment structure 526 to provide a second engagement force specific to a subsequent stage (e.g., second stage) of the treatment plan.

For example, the first appliance 587 can be placed over the jaw 596 of the patient and can be designed to interface with a first subset 528-2, 528-5 of surfaces 528-1 . . . 528-6 of the attachment structure 526. The interface can provide a first engagement force to move the at least one tooth 585 toward a first position that is specific to the first stage of the treatment plan and/or to minimize or prevent movement of and/or forces on the at least one tooth 585.

For example, the first engagement force can include a combination of forces 581, 583 (e.g., directional forces) provided by the first subset 528-2, 528-5 of surfaces 528-1 . . . 528-6 interfacing with the first appliance 587 (e.g., as illustrated by the direction of the arrows 581, 583). The first appliance 587 can include, for instance, one or more shapes 594-1, 594-2 designed to interface with the first subset 528-2, 528-5 of surfaces 528-1 . . . 528-6 (e.g., activated surfaces) when the first appliance 587 is worn over the jaw 596 by the patient.

FIG. 5B includes an illustration of the first appliance 587 when worn over the jaw of the patient. The attachment structure 526 attached to the tooth 585 can interface with the first appliance 587 to provide the first engagement force. For instance, the first appliance 587 can include a first shape 594-1 and a second shape 594-2. The shapes 594-1, 594-2 can interface with a first subset of surfaces (e.g., surfaces 528-2, 528-5 illustrated by FIG. 5A) to provide the first engagement force (e.g., the combination of forces 581, 583 illustrated by FIG. 5A), for example.

FIG. 5C includes an illustration of the second appliance 589 in the series of appliances 587, 589. The attachment structure 526, as illustrated by FIG. 5C, is attached to the same tooth 585 of the same jaw 596 as illustrated in FIG. 5A.

The second appliance 589 can be placed over the jaw 596 of the patient and can be designed to interface with a second subset 528-1, 528-3, 528-5 of surfaces 528-1 . . . 528-6 of the attachment structure 526. The interface can provide a second engagement force to move the at least one tooth 596 toward a second position that is specific to the second stage of the treatment plan and/or to minimize or prevent movement of and/or forces on the at least one tooth 585.

For instance, the second engagement force can include a combination of forces 591, 592, 593 (e.g., directional forces) provided by the second subset 528-1, 528-3, 528-5 of the surfaces 528-1 . . . 528-6 interfacing with the second appliance 589 (e.g., as illustrated by the direction of the arrows 591, 592, 593). For example, the second appliance 589 (e.g., second shell) can include one or more shapes 594-1, 594-2, 594-3 designed to interface with the second subset 528-1, 528-3, 528-5 of the surfaces 528-1 . . . 528-6 (e.g., activated surfaces) when the second appliance 589 is worn over the jaw 596 by the patient. In this manner, the attachment structure 526 can be used with multiple appliances (e.g., first appliance 587 and second appliance 589) to provide multiple engagement forces.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system, comprising:
    a first appliance of a series of appliances designed to incrementally implement a treatment plan, comprising a first shell having a plurality of cavities therein designed to receive teeth of a first jaw;
    an attachment structure designed to be attached to at least one tooth of the first jaw, wherein:
        the attachment structure includes a plurality of surfaces arranged about a center point of the attachment structure; and
        the first shell is designed to interface with a first surface of the plurality of surfaces to provide a first engagement force specific to a first stage of the treatment plan; and
    a second appliance of the series of appliances, comprising a second shell having a plurality of cavities therein designed to receive the teeth of the first jaw;
    wherein the second shell is designed to interface with a second surface of the plurality of surfaces of the attachment structure attached to the at least one tooth of the first jaw to provide a second engagement force specific to a second stage of the treatment plan.

2. The system of claim 1, wherein the first shell is designed to interface with a first subset of the plurality of surfaces to provide the first engagement force; and
    wherein the second shell is designed to interface with a second subset of the plurality of surfaces to provide the second engagement force.

3. The system of claim 2, wherein the first subset and the second subset include at least one surface that is different between them.

4. The system of claim 2, wherein the first subset and the second subset include at least one common surface between them.

5. The system of claim 1, wherein the first shell is designed to interface with the first surface to provide the first engagement force to move the at least one tooth toward a first position that is specific to the first stage of the treatment plan.

6. The system of claim 1, wherein the second shell is designed to interface with the second surface to provide the second engagement force to move the at least one tooth toward a second position that is specific to the second stage of the treatment plan.

7. The system of claim 1, wherein the series of appliances includes a third appliance comprising a third shell having a plurality of cavities therein designed to receive teeth of a second jaw during the first stage of the treatment plan.

8. The system of claim 7, wherein the attachment structure attached to at least one tooth of the first jaw comprises a first attachment structure, and wherein the system includes a second attachment structure designed to be attached to at least one tooth of the second jaw, wherein the second attachment structure includes a plurality of surfaces; and
    wherein the third shell is designed to interface with a first surface of the plurality of surfaces to provide a third engagement force specific to the first stage of the treatment plan.

9. The system of claim 1, wherein the attachment structure is attached to the at least one tooth of the first jaw such that each of the plurality of surfaces designed to apply a force thereto in a variety of orientations to provide a variety of engagement forces.

10. A non-transitory computing device readable medium having instructions stored thereon that are executable by a processor to cause a computing device to:
- position an attachment structure on at least one virtual tooth of a virtual model of a jaw, wherein the attachment structure includes a plurality of surfaces arranged about a center point of the attachment structure;
- activate a first subset of the plurality of surfaces of the attachment structure at a first stage of a treatment plan that is incremented in stages;
- activate a second subset of the plurality of surfaces of the attachment structure at a second stage of the treatment plan according to changes to the virtual model of the jaw between the first stage of the treatment plan and the second stage of the treatment plan; and
- provide the virtual model of the jaw for fabrication of physical models corresponding to the jaw at the first and the second stages of the treatment plan for formation of appliances thereover such that the appliances includes a shape designed to interface with the activated surfaces of the attachment structure.

11. The medium of claim 10, wherein an appliance that includes the shape designed to interface the activated surfaces includes a surface designed to interface with the activated surfaces.

12. The medium of claim 10, including instructions to:
- model a first engagement force to be applied by the first subset of the plurality of surfaces of the attachment structure interfacing with a corresponding one of the appliances during the first stage of the treatment plan; and
- model a second engagement force to be applied by the second subset of the plurality of surfaces of the attachment structure interfacing with a corresponding one of the appliances during the second stage of the treatment plan.

13. The medium of claim 12, including instructions to revise at least one of a shape, a location, and an orientation of the attachment structure based on at least one of the modeled first engagement force and the modeled second engagement force.

14. The medium of claim 10, wherein the instructions to activate the first subset of the plurality of surfaces incorporate a result of instructions to model a first number of forces used to reposition the corresponding at least one virtual tooth a first distance according to the first stage of the treatment plan.

15. The medium of claim 14, wherein the instructions to activate the second subset of the plurality of surfaces to incorporate a result of instructions to model a second number of forces used to reposition the corresponding at least one virtual tooth a second distance according to the second stage of the treatment plan.

16. A system, comprising:
- a first appliance of a series of appliances designed to incrementally implement a treatment plan, comprising a first shell having a plurality of cavities therein designed to receive teeth of a jaw in a first stage of the treatment plan;
- an attachment structure designed to be attached to at least one tooth of the jaw, wherein:
  - the attachment structure includes a plurality of surfaces arranged about a center point of the attachment structure; and
  - the first shell is designed to interface with a first subset of the plurality of surfaces of the attachment structure to provide a first engagement force specific to the first stage of the treatment plan; and
- a second appliance of the series of appliances, comprising a second shell having a plurality of cavities therein designed to receive teeth of the jaw in a second stage of the treatment plan;
- wherein the second shell is designed to interface with a second subset of the plurality of surfaces to provide a second engagement force specific to a second stage of the treatment plan, and wherein the first engagement force and the second engagement force include different forces.

17. The system of claim 16, wherein the first engagement force and the second engagement force include at least one of a rotational force and a linear force.

18. The system of claim 16, wherein the plurality of surfaces of the attachment structure include at least three surfaces.

19. The system of claim 16, wherein:
- the attachment structure includes a geometric shape; and
- the plurality of surfaces of the attachment structure include surfaces that are oriented normal to one another about the geometric shape.

20. The system of claim 16, wherein:
- the attachment structure includes a plurality of attachment structure components each individually designed to be attached to the at least one tooth, the plurality of attachment structures forming a geometric shape on the at least one tooth; and
- the plurality of surfaces of the attachment structure include surfaces that are oriented normal to one another about the geometric shape formed by the plurality of attachment structure components.

* * * * *

UNITED STATES PATENT AND TRADEMARK OFFICE
CERTIFICATE OF CORRECTION

PATENT NO. : 9,700,385 B2
APPLICATION NO. : 14/466734
DATED : July 11, 2017
INVENTOR(S) : Peter Webber It is certified that error appears in the above-identified patent and that said Letters Patent is hereby corrected as shown below:

On the Title Page

Item (73), Line 1, "Alitn" should read "Align".

Signed and Sealed this
Nineteenth Day of December, 2017

Joseph Matal
*Performing the Functions and Duties of the
Under Secretary of Commerce for Intellectual Property and
Director of the United States Patent and Trademark Office*